United States Patent [19]

Rialdi

[11] 4,181,712

[45] Jan. 1, 1980

[54] TOOTH PASTE COMPOSITION

[76] Inventor: Giorgio Rialdi, 18, Via P. Semeria, I-16131 Genova, Italy

[21] Appl. No.: 938,493

[22] Filed: Aug. 31, 1978

Related U.S. Application Data

[63] Continuation-in-part of Ser. No. 768,199, Feb. 14, 1977, abandoned.

[51] Int. Cl.$^2$ .......................... A61K 7/16; A61K 7/26; A61K 33/44
[52] U.S. Cl. .......................... 424/49; 424/58; 424/125
[58] Field of Search .................. 424/48–58, 424/125

[56] References Cited

U.S. PATENT DOCUMENTS

| 69,393 | 10/1867 | Blake | 424/58 |
|---|---|---|---|
| 1,467,024 | 9/1923 | Bergve | 424/49 |
| 1,484,415 | 2/1924 | Shepherd | 424/51 |
| 1,523,840 | 1/1925 | Schlesinger | 424/58 |
| 1,567,974 | 12/1925 | Monroe | 424/94 |
| 1,716,035 | 6/1929 | Donchi | 424/58 |
| 1,943,467 | 1/1934 | Bley | 424/50 |
| 1,947,635 | 2/1934 | Bergve | 424/49 |
| 2,154,168 | 4/1939 | Klein et al. | 424/50 |
| 2,689,170 | 9/1954 | King | 424/54 |
| 3,538,230 | 11/1970 | Pador et al. | 424/54 |

FOREIGN PATENT DOCUMENTS 676972 12/1963 Canada .
964499 8/1950 France .
2791M 9/1964 France .
205363 6/1939 Switzerland .

*Primary Examiner*—Shep K. Rose
*Attorney, Agent, or Firm*—Spencer & Kaye

[57] ABSTRACT

A tooth paste composition comprising, in combination with a detergent base, a mixture of micronized colloidal silica gel and activated charcoal.

6 Claims, No Drawings

TOOTH PASTE COMPOSITION

PRIOR RELATED APPLICATION

This application is a continuation-in-part of my prior U.S. Pat. application Ser. No. 768,199 filed Feb. 14, 1977.

PRIOR ART STATEMENT

The following prior art is known to the applicant:

| U.S. Pat. No. | Date of Issue | Inventors |
| --- | --- | --- |
| 3,935,306 | Jan. 27, 1976 | Roberts et al. |
| 1,523,840 | Jan. 20, 1925 | Schlesinger |
| 3,978,205 | Aug. 31, 1976 | Newman et al. |
| 3,535,420 | Oct. 20, 1970 | McCune et al. |
| 1,716,035 | June 4, 1929 | Donchi |

| British Patent No. | Date of Issue | Inventors |
| --- | --- | --- |
| 1,186,706 | April 2, 1970 | Morton et al. |
| 1,033,229 | June 22, 1966 | Aptor |
| 423,858 | Feb. 11, 1935 | Haddan |
| 457,270 | Nov. 24, 1936 | Messner |

Canadian Pat. No. 676,972 issued Dec. 31, 1963 to MacIntosh Scott
German OLS No. 2409755 Published Sept. 11, 1975 to Raaf et al.
French Pat No. 902,729 issued July 2, 1962 to Meyer
Swiss Pat. No. 205,363 published Sept. 1, 1939 to Herzog Jordan W. A. et al., J. Am. Dent. Assoc. 54/589 (1957 Accepted Dental Therapeutics, 35th edition p. 253-256).

BACKGROUND OF THE INVENTION

This invention relates to a tooth paste composition containing a mixture of hydratated colloidal silica gel and activated charcoal having a particle size of between 0.2 and 0.3 microns, dispersed into a detergent base which does not contain any abrasives. The said composition has a good detergent and whitening action on the teeth without any detrimental effect on the tooth enamel.

DESCRIPTION OF THE PRIOR ART

The Roberts et al. patent (U.S. Pat. No. 3,935,306) relates to a tooth paste composition containing a gel vehicle having dispersed therein a polishing agent. The polishing agents of Roberts et al. provide cleaning and polishing functions. Roberts et al. disclose, at column 2, a large number of suitable polishing agents and state that they suitably can have a particle size of between 0.1 and 10 microns. At column 5, Roberts et al. provide a detailed discussion of the use of silica as a polishing agent, and state at column 5, lines 23 and 24 that the siliceous material preferably have a particle size between 1 and 20 microns. Various other materials, such as surfactants, coloring agents, preservatives, antibacterial agents and so on can be incorporated in the composition. The Roberts et al. patent does not suggest that a tooth paste composition should be free of abrasives, does not disclose or suggest the use of charcoal, and does not disclose or suggest the use of a mixture of charcoal and a colloidal silica, which mixture has no abrasive effect.

The German Patent to Raaf et al. (German OLS No. 2409755) discloses that tooth paste compositions containing finely divided silica as the main cleansing agent have an insufficient cleansing character, which Raaf et al. state probably is due to the lack of abrasion effect. See page 2, lines 6 to 9 from the bottom, which, in translation, read as follows:

"It has been found, however, that when using toothpastes containing finely distributed silicon dioxide as the major polishing agent component, a dark coating appears on the teeth of the user soon after use which probably is due to lack of abrasion effect of such toothpastes." This insufficiency of the known tooth paste compositions is avoided by Raaf et al. by adding urea. Thus, Raaf et al. recognize that finely divided silica does not have a cleaning and abrasive effect and turn to the use of urea to provide a cleansing effect. Raaf et al. contain absolutely no suggestion that a combination of silica with charcoal can overcome the problem, and teach away from the solution of the present invention since they rely on urea to overcome the problem.

The British Pat. No. 1,186,706 to Pader et al. uses a tooth paste composition containing as the "sole or principal" cleansing agent a dehydrated silica gel having an average particle diameter of from 2 to 20 microns. Pader et al. disclose that the composition can further contain a synthetic silica which has thickening and gelling properties, but which has no cleansing ability and which does not remove stains. The Pader et al. patent contains absolutely no teaching or suggestion of a composition which does not contain abrasive but which contains a mixture of charcoal and silica.

The Schlesinger Patent (U.S. Pat. No. 1,523,840) relates to a tooth paste composition containing finely pulverized charcoal in combination with a mineral oil, together with flavoring ingredients. Schlesinger discloses that his tooth paste can contain such ingredients as precipitated chalk. Precipitated chalk, of course, is calcium carbonate, and calcium carbonate is a conventional abrasive. Schlesinger does not disclose the particle size of his charcoal, and does not disclose or suggest that it should be used in combination with silica in a tooth paste composition which does not contain abrasives.

The Canadian Pat. No. 676,972 is concerned with a tooth paste composition containing filler material which can provide an abrasive action, foaming agents, binders, flavoring agents and water, and finely divided carbon particles of a size ranging from 80 to 200 microns. As disclosed at page 3, lines 23 to 25, the carbon particles provide an abrasive action, and as disclosed at page 4, lines 20 to 23, the particle size of the charcoal should be at least 80 microns to provide the abrasive effect.

The French Pat. No. 902,729 relates to a tooth paste composition containing charcoal. This patent, however does not disclose the particle size of the charcoal and contains absolutely no disclosure or suggestion of using the charcoal in combination with silica.

The Swiss Pat. No. 205,363 relates to a tooth paste composition containing charcoal as cleansing, disinfectact and absorbing agent. The Swiss Patent does not indicate the size of the charcoal and does not indicate that it should be combined with silica to provide an effective tooth paste composition.

The British Pat. No. 457,270 relates to chewable hollow containers or capsules adapted to contain a small charge of a mouth medicament. According to the said patent, the construction of containers of a paraffin composition has been made possible by the discovery that certain fillers, when added to paraffin, will increase its natural softening point by several degrees (page 2, column 1, lines 55 to 59 and following). Among the fillers useful for the invention silica and adsorbent carbon are mentioned. The said fillers are utilized in finely divided dry or substantially dry form. The particle size of said fillers is defined as such which will pass a 100 mesh to a 400 mesh sieve, 200 mesh material being preferable.

The U.S. Pat. No. 1,716,035 to Donchi relates to a tooth paste composition containing, in addition to other usual ingredients, also activated vegetable carbon and kieselguhr. This patent, however does not disclose the particle size of the carbon, whilst the kieselguhr is composed by non gellyfying silica of a grain size of about 90 to 160 microns×1.5 to 4.6 microns that is far distant from the size range recited in my invention.

SUMMARY OF THE INVENTION

It is therefore the main object of the present invention to provide a tooth paste composition which obviates to the disadvantages of the known compositions containing abrasives, or abrading substances.

According to the invention, this object is obtained by a tooth paste composition which does not contain any abrasives, and which contains a detergent base and a mixture of colloidal silica gel and activated charcoal having a particle size of between 0.2 and 0.3 microns. By the term "detergent base" a composition is intended containing humectants, binders, flavoring agent, germicidal agents and detergents, which are conventional ingredients in a tooth paste composition, with the exclusion of abrasives.

Surprisingly, it has been discovered that by forming a tooth paste composition containing a detergent base, as above defined, and further admixing to the said detergent base a hydratated mixture of colloidal silica gel and charcoal having the above defined particle size, a tooth paste composition with excellent cleansing ability exempt from damaging abrasive effects is obtained, and this against the general opinion that either silica or carbon at the very reduced particle size have no abrasive and therefore no cleansing effect.

Thanks to the adsorbing properties of the charcoal, the above association may adsorb the fermentation products and the acidity from the sugars, thus explaining together with the cleansing and whitening action also a caries prophylaxis action.

EXAMPLE

The following is an example of tooth paste composition according to the invention. In the example the amounts are expressed in percent by weight.

| | | |
|---|---|---|
| Humectants | Glycerine | 7% |
| | Sorbitol | 21% |
| Detergents | Sodium lauryl sulfate | 2% |
| | Sodium lauroyl-sarcosinate | 1% |
| Aromatic improver | Peppermint oil | 2% |
| | Glycyrrhiza | 6% |
| Germicidal: Undebenzofene | | 1.5% |
| Flavoring agent: Glycyrrhizzin | | 0.5% |
| Water, demineralized | | 53% |
| Carbo-silica colloidal gel | | 6% |
| | | 100.00% |

The carbo-silica colloidal gel of the Example was formed by admixing into a suitable colloidal mill 1 part by weight of activated charcoal with 9 parts by weight of silica, and by milling this mixture until a grain size of 0,2 microns was obtained. The mixture was transformed into a colloidal gel by adding thereto an amount of water corresponding to the 150% in weight of the mixture. Thus, 100 grams of the carbo-silica colloidal gel of the Example are composed by 4 grams of carbon, 36 grams of silica and 60 grams of water. This means that in the composition of the Example, the silica is contained in an amount of 2.16% in weight of the composition and the carbon in an amount of 0.24% of the composition. The ratio between carbon and silica in the carbo-silica colloidal gel may vary from 1 part carbon to 20 parts silica to 1 part carbon to 2 parts silica, with the preferred ratio being comprised between 1:8 and 1:10. The total amount of carbo-silica colloidal gel in the composition may vary between 3% to 9% in weight, based on the total weight of the composition, the preferred amount being comprised between 4,8% and 6%. The carbo-silica colloidal gel mixture may contain from about 40% to about 80% by weight, and preferably about 60% by weight of demineralized water. The tooth paste composition contains from 50 to 55% by weight of demineralized water.

As germicidal, any suitable germicidal may be used, although undebenzofene, a paraoxybenzoic derivative of the ethyleneglycolphenylundecylether having the formula

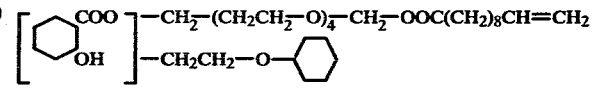

has shown excellent germicidal properties in a tooth paste composition.

Advantageously, as aromatic improver glycyrrhizin is used, which exert also a beneficial effect on the stability of the tooth paste composition.

I claim:

1. A tooth paste composition comprising in combination:
   (a) from 91 to 97% by weight, based on the weight of the tooth paste composition, of a detergent base; and
   (b) from 3–9% by weight of a mixture of micronized colloidal silica gel and activated charcoal of a grain size of from 0.2 to 0.3 microns; said detergent base comprising from 1 to 3% by weight, based on the weight of the tooth paste composition, of a detergent, from 23 to 28% of an humectant, from 6 to 9% of flavoring agents and aromatic improvers, from 0.5 to 1.5% of a germicidal agent, and from 50 to 55% demineralized water; and said silica and said charcoal being contained in said mixture thereof in a ratio of from about 1 part of carbon to 2 parts of silica to about 1 part of carbon to 20 parts of silica, with said mixture containing from about 40 to about 80% by weight of demineralized water.

2. A composition according to claim 1, in which said mixture of colloidal silica and activated charcoal is present in a ratio of 1 part of carbon to 9 parts of silica, with said mixture containing about 60% by weight of demineralized water.

3. A composition according to claim 1, in which said flavoring agents and aromatic improvers include glycyrrhizin which exerts also a beneficial effect on the stability of the composition.

4. A composition according to claim 1, in which said germicidal agent comprises a paraoxybenzoic derivative of ethyleneglycolphenylundecylether having the formula:

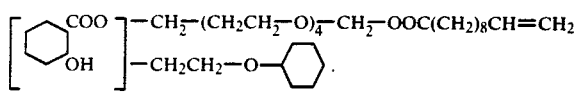

5. A composition according to claim 1, in which the ratio of carbon to silica in said mixture is from about 1 part carbon to 8 parts silica to about 1 part carbon to 10 parts silica.

6. A composition according to claim 5, in which said colloidal mixture contains about 60% by weight of demineralized water.

* * * * *